United States Patent
Boor et al.

(10) Patent No.: US 11,478,644 B2
(45) Date of Patent: Oct. 25, 2022

(54) SYSTEMS AND METHODS FOR DC PROTECTION IN IMPLANTABLE PULSE GENERATORS

(71) Applicant: Advanced Neuromodulation Systems, Inc., Plano, TX (US)

(72) Inventors: Steven Boor, Plano, TX (US); Daran DeShazo, Lewisville, TX (US)

(73) Assignee: ADVANCED NEUROMODULATION SYSTEMS, INC., Plano, TX (US)

( * ) Notice: Subject to any disclaimer, the term of this patent is extended or adjusted under 35 U.S.C. 154(b) by 171 days.

(21) Appl. No.: 16/855,212

(22) Filed: Apr. 22, 2020

(65) Prior Publication Data
US 2021/0330978 A1  Oct. 28, 2021

(51) Int. Cl.
*A61N 1/36* (2006.01)
*A61N 1/375* (2006.01)
*A61N 1/39* (2006.01)

(52) U.S. Cl.
CPC ..... *A61N 1/36125* (2013.01); *A61N 1/36067* (2013.01); *A61N 1/36071* (2013.01); *A61N 1/36142* (2013.01); *A61N 1/3758* (2013.01); *A61N 1/3925* (2013.01); *A61N 1/3968* (2013.01)

(58) Field of Classification Search
CPC .... A61N 1/36125; A61N 1/3758; A61N 1/08; A61N 1/3925; A61N 1/3968; A61N 1/36142
See application file for complete search history.

(56) References Cited

U.S. PATENT DOCUMENTS

| | | |
|---|---|---|
| 7,024,246 B2 | 4/2006 | Acosta et al. |
| 7,715,912 B2 | 5/2010 | Rezai et al. |
| 8,082,033 B2 | 12/2011 | Rezai et al. |
| 8,515,545 B2 | 8/2013 | Trier |
| 8,560,060 B2 | 10/2013 | Donofrio et al. |
| 9,008,790 B2 | 4/2015 | Griffith et al. |
| 9,079,036 B2 | 7/2015 | Wanasek |
| 9,144,687 B2 | 9/2015 | Griffith et al. |
| 9,278,229 B1 | 3/2016 | Reinke et al. |
| 9,457,192 B2 | 10/2016 | Birkholz et al. |

(Continued)

OTHER PUBLICATIONS

International Search Report and Written Opinion for International Patent Application No. PCT/US2021/028337, dated Jul. 7, 2021, 12 pages.

*Primary Examiner* — Paula J Stice
(74) *Attorney, Agent, or Firm* — Armstrong Teasdale LLP

(57) ABSTRACT

The present disclosure provides systems and methods for circuitry for an implantable pulse generator (IPG) of a neurostimulation system. The circuitry includes at least one anode node, at least one cathode node, a plurality of switching circuits, each switching circuit coupled to the at least one anode node and the at least one cathode node, and a plurality of output channels, each output channel coupled between an associated switching circuit and at least one electrode. The circuitry further includes a first DC blocking capacitor coupled between the at least one anode node and the plurality of switching circuits, a second DC blocking capacitor coupled between the at least one cathode node and the plurality of switching circuits. The circuitry further includes mitigation circuitry operable to limit DC leakage from the plurality of switching circuits through the plurality of output channels.

20 Claims, 7 Drawing Sheets

(56) References Cited

U.S. PATENT DOCUMENTS

| | | |
|---|---|---|
| 9,474,905 B2 | 10/2016 | Doan et al. |
| 9,656,084 B2 | 5/2017 | Mcdonald et al. |
| 10,226,197 B2 | 3/2019 | Reinke et al. |
| 2005/0245970 A1 | 11/2005 | Erickson et al. |
| 2010/0268309 A1 | 10/2010 | Parramon et al. |
| 2016/0144183 A1 | 5/2016 | Marnfeldt et al. |

SYSTEMS AND METHODS FOR DC PROTECTION IN IMPLANTABLE PULSE GENERATORS

FIELD OF THE DISCLOSURE

The present disclosure relates generally to neurostimulation systems, and more particularly to providing more area efficient and effective direct current (DC) protection in implantable pulse generators.

BACKGROUND ART

Neurostimulation is an established neuromodulation therapy for the treatment of chronic pain and movement disorders. For example, neurostimulation has been shown to improve cardinal motor symptoms of Parkinson's Disease (PD), such as bradykinesia, rigidity, and tremors. Types of neurostimulation include deep brain stimulation (DBS), spinal cord stimulation (SCS), and Dorsal Root Ganglion (DRG) stimulation.

Neurostimulation systems typically include an implantable pulse generator (IPG). In IPGs, to prevent potential tissue damage and electrode corrosion, it is desirable to protect against DC from reaching patient tissue. Accordingly, hardware mitigations are generally implemented to protect against single-fault failures in IPG circuitry.

For example, DC blocking capacitors may be used to prevent DC from reaching electrodes and patient tissue. Specifically, these capacitors block DC, and only conduct dynamic (i.e., alternating current (AC) signals). In at least some known systems, for each output channel of a neurostimulator IPG (e.g., for sixteen different output channels), a DC blocking capacitor is connected in series with each output channel. Notably, to function properly, DC blocking capacitors have a relatively high capacitance (e.g., 22 microfarads (µF)) and may have a relatively large device footprint. Accordingly, including a DC blocking capacitor for each output channel may be relatively expensive and may make it difficult to reduce the size of an IPG (which is generally desirable).

Accordingly, it would be desirable to provide an IPG that ensures DC protection with a reduced number of DC blocking capacitors, and that implements improved DC protection techniques.

BRIEF SUMMARY OF THE DISCLOSURE

In one embodiment, the present disclosure is directed to circuitry for an implantable pulse generator (IPG) of a neurostimulation system. The circuitry includes at least one anode node, at least one cathode node, a plurality of switching circuits, each switching circuit coupled to the at least one anode node and the at least one cathode node, and a plurality of output channels, each output channel coupled between an associated switching circuit and at least one electrode. The circuitry further includes a first DC blocking capacitor coupled between the at least one anode node and the plurality of switching circuits, a second DC blocking capacitor coupled between the at least one cathode node and the plurality of switching circuits. The circuitry further includes mitigation circuitry operable to limit DC leakage from the plurality of switching circuits through the plurality of output channels.

In another embodiment, the present disclosure is directed to a neurostimulation system. The neurostimulation system includes an implantable pulse generator (IPG) ground, an IPG case, a stimulation lead comprising a plurality of electrodes, and an IPG coupled to the IPG ground, the IPG case, and the stimulation lead. The IPG includes circuitry that includes at least one anode node, at least one cathode node, a plurality of switching circuits, each switching circuit coupled to the at least one anode node and the at least one cathode node, and a plurality of output channels, each output channel coupled between an associated switching circuit and at least one electrode. The circuitry further includes a first DC blocking capacitor coupled between the at least one anode node and the plurality of switching circuits, a second DC blocking capacitor coupled between the at least one cathode node and the plurality of switching circuits. The circuitry further includes mitigation circuitry operable to limit DC leakage from the plurality of switching circuits through the plurality of output channels.

In another embodiment, the present disclosure is directed to a method of assembling circuitry for an implantable pulse generator (IPG) of a neurostimulation system including an IPG ground, a plurality of electrodes, and an IPG case. The method includes providing at least one anode node and at least one cathode node, electrically coupling a plurality of switching devices to the at least one anode node and the at least one cathode node, and electrically coupling each of a plurality of output channels between an associated switching device and at least one electrode. The method further includes electrically coupling a first DC blocking capacitor between the at least one anode node and the plurality of switching circuits, electrically coupling a second DC blocking capacitor between the at least one cathode node and the plurality of switching circuits, and implementing migration circuitry operable to limit DC leakage from the plurality of switching circuits through the plurality of output channels.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

Figure 1:
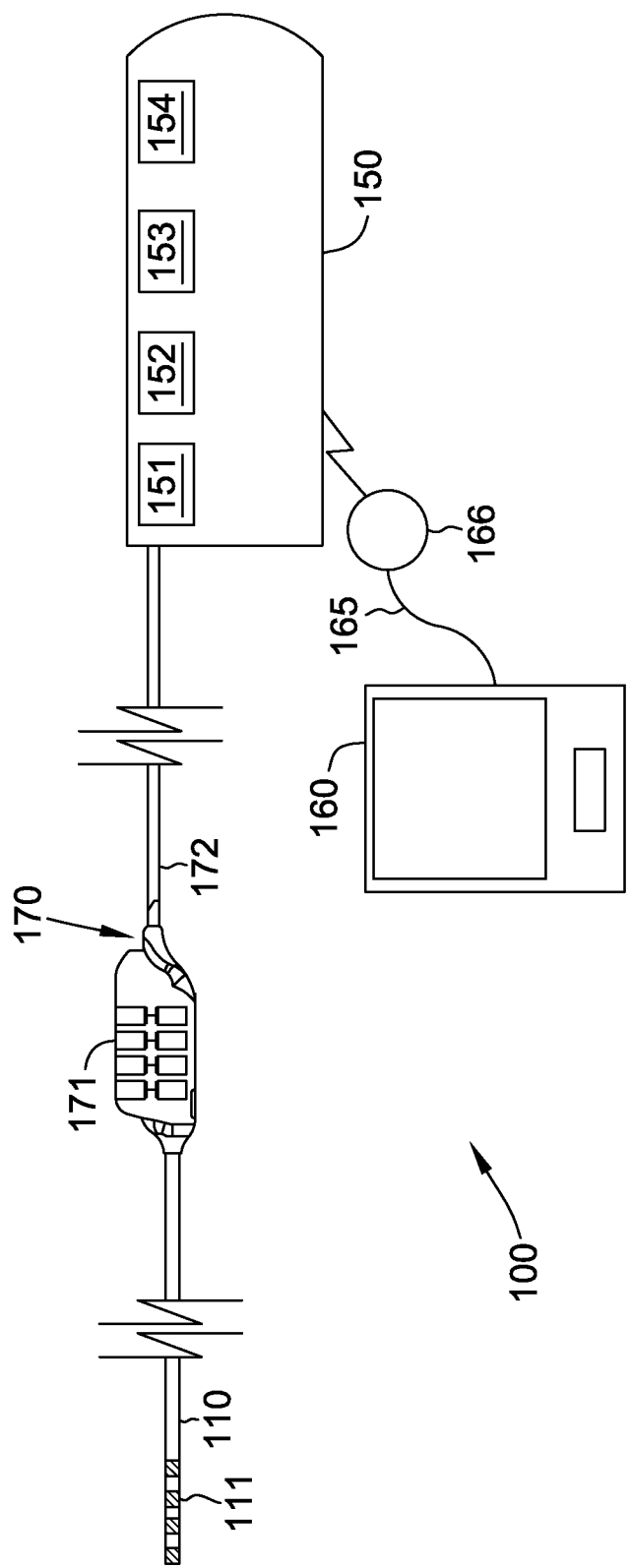
FIG. 1 is a schematic view of one embodiment of a stimulation system.

The present disclosure provides systems and methods for improved circuitry for an implantable pulse generator (IPG) of a neurostimulation system. The circuitry includes at least one anode node, at least one cathode node, a plurality of switching circuits, each switching circuit coupled to the at least one anode node and the at least one cathode node, and a plurality of output channels, each output channel coupled between an associated switching circuit and at least one electrode. The circuitry further includes a first DC blocking capacitor coupled between the at least one anode node and the plurality of switching circuits, and a second DC blocking capacitor coupled between the at least one cathode node and the plurality of switching circuits. The circuitry further includes mitigation circuitry operable to limit DC leakage from the plurality of switching circuits through the plurality of output channels.

The improved IPG circuitry described herein reduces the number of DC blocking capacitors needed to provide DC protection by coupling the DC blocking capacitors between anode/cathode nodes and switching circuitry of the IPG, instead of between the switching circuitry and electrodes of the IPG. This allows for a reduced number of DC blocking capacitors, reducing the cost, size, and complexity of the IPG. Reducing the number of components also reduces risks due to component failure.

Further, the improved IPG circuitry described herein facilitates mitigating potential DC leakage that may result from locating the DC blocking capacitors between the anode/cathode nodes and the switching circuitry of the IPG. That is, the embodiments described herein ensure that only safe levels of DC leakage (e.g., well below 1 microamp ($\mu$A)) occur in output channels of the IPG under single fault conditions.

Neurostimulation systems are devices that generate electrical pulses and deliver the pulses to nervous tissue of a patient to treat a variety of disorders. One category of neurostimulation systems is deep brain stimulation (DBS). In DBS, pulses of electrical current are delivered to target regions of a subject's brain, for example, for the treatment of movement and effective disorders such as PD and essential tremor. Another category of neurostimulation systems is spinal cord stimulation (SCS) which is often used to treat chronic pain such as Failed Back Surgery Syndrome (FBSS) and Complex Regional Pain Syndrome (CRPS).

Neurostimulation systems generally include a pulse generator and one or more leads. A stimulation lead includes a lead body of insulative material that encloses wire conductors. The distal end of the stimulation lead includes multiple electrodes, or contacts, that intimately impinge upon patient tissue and are electrically coupled to the wire conductors. The proximal end of the lead body includes multiple terminals (also electrically coupled to the wire conductors) that are adapted to receive electrical pulses. In DBS systems, the distal end of the stimulation lead is implanted within the brain tissue to deliver the electrical pulses. The stimulation leads are then tunneled to another location within the patient's body to be electrically connected with a pulse generator or, alternatively, to an "extension." The pulse generator is typically implanted in the patient within a subcutaneous pocket created during the implantation procedure.

The pulse generator is typically implemented using a metallic housing (or can) that encloses circuitry for generating the electrical stimulation pulses, control circuitry, communication circuitry, a rechargeable or primary cell battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on the proximal end of a stimulation lead.

Referring now to the drawings, and in particular to FIG. 1, a stimulation system is indicated generally at 100. Stimulation system 100 generates electrical pulses for application to tissue of a patient, or subject, according to one embodiment. System 100 includes an implantable pulse generator (IPG) 150 that is adapted to generate electrical pulses for application to tissue of a patient. Alternatively, system 100 may include an external pulse generator (EPG) positioned outside the patient's body. IPG 150 typically includes a metallic housing (or can) that encloses a controller 151, pulse generating circuitry 152, a battery 153, far-field and/or near field communication circuitry 154, and other appropriate circuitry and components of the device. Controller 151 typically includes a microcontroller or other suitable processor for controlling the various other components of the device. Software code is typically stored in memory of IPG 150 for execution by the microcontroller or processor to control the various components of the device.

IPG 150 may comprise one or more attached extension components 170 or be connected to one or more separate extension components 170. Alternatively, one or more stimulation leads 110 may be connected directly to IPG 150. Within IPG 150, electrical pulses are generated by pulse generating circuitry 152 and are provided to switching circuitry. The switching circuit connects to output wires, traces, lines, or the like (not shown) which are, in turn, electrically coupled to internal conductive wires (not shown) of a lead body 172 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from IPG 150 and conducted through the conductors of lead body 172 are provided to stimulation lead 110. The pulses are then conducted through the conductors of lead 110 and applied to tissue of a patient via electrodes 111. Any suitable known or later developed design may be employed for connector portion 171.

For implementation of the components within IPG 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within IPG 150. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may include a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number and type of electrodes 111, terminals, and internal conductors.

Controller device 160 may be implemented to recharge battery 153 of IPG 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller device 160 generates an AC-signal to drive current through coil 166 of wand 165. Assuming that primary coil 166 and secondary coil are suitably positioned relative to each other, the secondary coil is disposed within the magnetic field generated by the current driven through primary coil 166. Current is then induced by a magnetic field in the secondary coil. The current induced in the coil of the implantable pulse generator is rectified and regulated to recharge the battery of IPG 150. The charging circuitry may also communicate status messages to controller device 160 during charging operations using pulse-loading or any other suitable technique. For example, controller device 160 may communicate the coupling status, charging status, charge completion status, etc.

External controller device 160 is also a device that permits the operations of IPG 150 to be controlled by a user after IPG 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 150.

Controller device 160 preferably provides one or more user interfaces to allow the user to operate IPG 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. In the methods and systems described herein, stimulation parameters may include, for example, a number of pulses in a burst (e.g., 3, 4, or 5 pulses per burst), an intra-burst frequency (e.g., 500 Hz), an inter-burst frequency (e.g., 40 Hz), and a delay between the pulses in a burst (e.g., less than 1 millisecond (ms)).

IPG 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference. Example commercially available neurostimulation systems include the EON MINI™ pulse generator and RAPID PROGRAMMER™ device from Abbott Laboratories.

The systems and methods described herein reduce the number of DC blocking capacitors needed to provide DC protection Further, the embodiments described herein facilitate ensuring that only safe levels of DC leakage occur in output channels of IPG 150 under single fault conditions. The systems and methods described herein are particularly useful in SCS systems, but may also be used in other neurostimulation systems (e.g., DBS or DRG systems).

Figure 2:
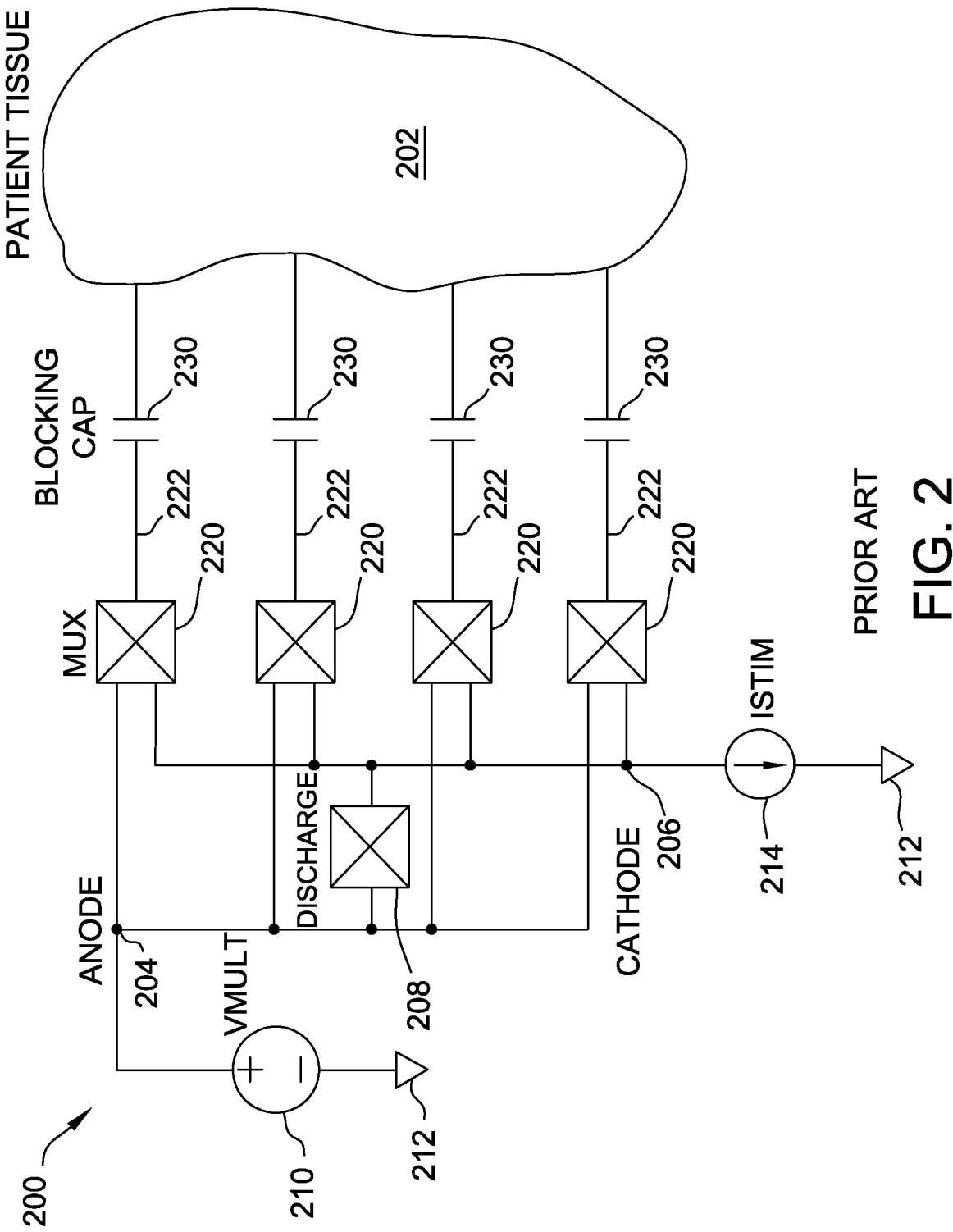
FIG. 2 is a circuit diagram of known implantable pulse generator (IPG) circuitry for applying stimulation to patient tissue.

FIG. 2 is a circuit diagram of known IPG circuitry 200 for applying stimulation to patient tissue 202. IPG circuitry 200 includes at least one anode node 204, at least one cathode node 206, and discharge circuitry 208 coupled between at least one anode node 204 and at least one cathode node 206. Further, a voltage source 210 is coupled between anode node 204 and ground 212, and a current source 214 is coupled between cathode node 206 and ground 212.

As shown in FIG. 2, in known IPG circuitry 200, anode node 204 and cathode node 206 are each directly coupled to a plurality of switching circuits 220. Further, each switching circuit 220 is coupled to a corresponding output channel 222. To apply stimulation to patient tissue 202, a current flows from anode node 204 to cathode node 206, and switching circuits 220 selectively deliver stimulation current through output channels 222. More specifically, the current flowing from anode node 204 to cathode node 206 is generated by producing a voltage at anode node 204 for a predefined period of time and sinking the current at cathode node 206 for the same predefined period of time. The predefined period of time corresponds to the pulse width for the applied stimulation. Anode node 204 and cathode node 206 are tri-stated (i.e., floating) outside of the predetermined period of time.

Between stimulation pulses, current can be discharged passively using discharge circuitry 208. For example, passive discharge may be achieved by shorting anode node 204 to cathode node 206 between stimulation pulses. This allows charge built up on the electrodes during stimulation to be discharged, which prevents electrode corrosion and other possible deleterious conditions for the patient. Active discharge can also be utilized for electrode discharge by inverting the behavior of switching circuits 220 so that current flow is reversed.

To provide DC protection, in known IPG circuitry 200, each output channel 222 is coupled in series with an associated DC blocking capacitor 230. That is, one DC blocking capacitor 230 is coupled between each switching circuit 220 and patient tissue 202. DC blocking capacitors 230 prevent any DC current flowing from switching circuits 220 from reaching patient tissue 202. In the embodiment shown in FIG. 2, known IPG circuitry 200 includes four switching circuits 220. Accordingly, four DC blocking capacitors 230 are required in this configuration.

Figure 3:
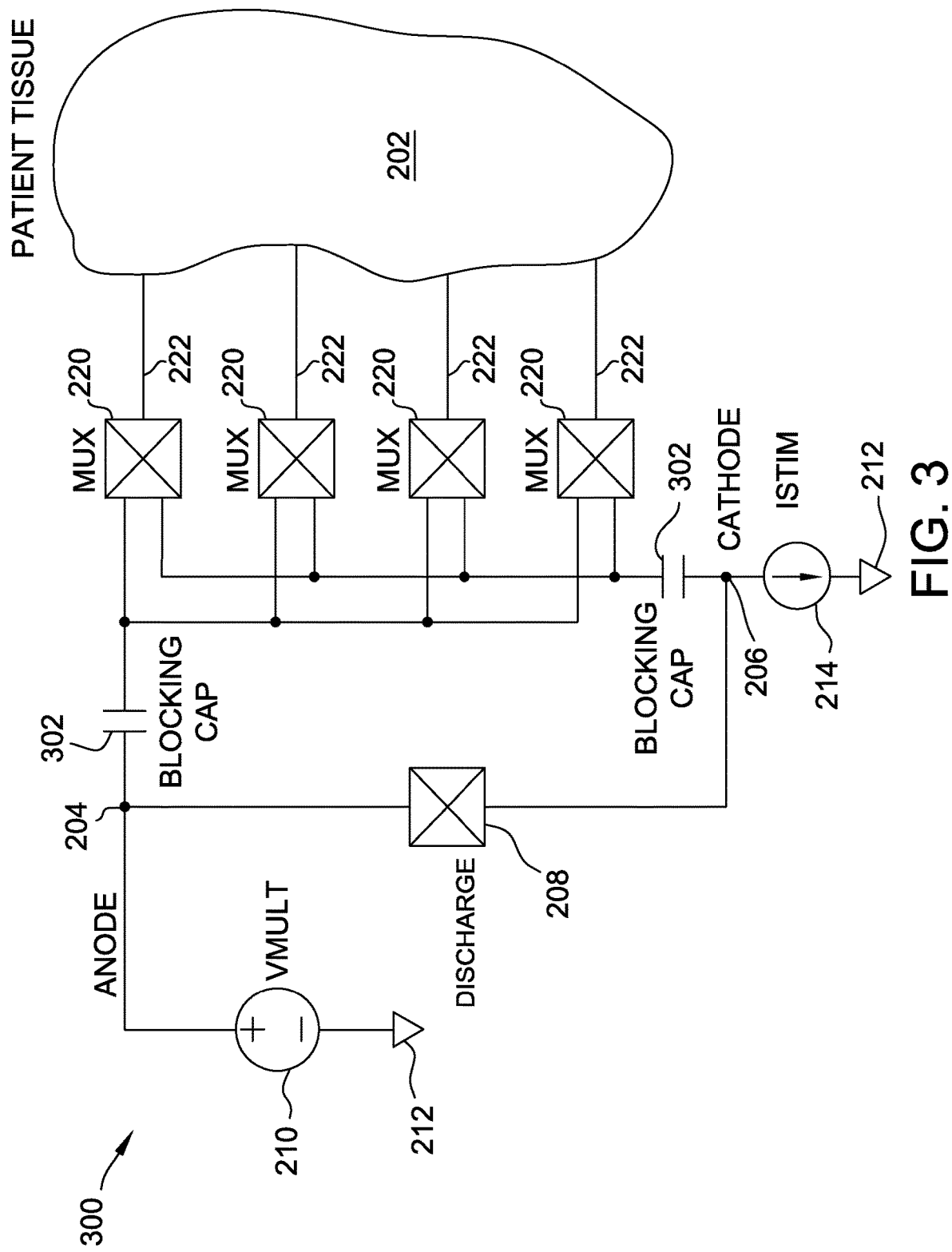
FIG. 3 is a circuit diagram of one embodiment of IPG circuitry in accordance with the present disclosure.

FIG. 3 is a circuit diagram of one embodiment of IPG circuitry 300 in accordance with the present disclosure. Unless otherwise indicated, components in IPG circuitry 300 are substantially similar to components in known IPG circuitry 200 given the same reference numeral. In contrast to known IPG circuitry 200, in IPG circuitry 300, DC blocking capacitors 302 are connected between anode node 204/cathode node 206 and switching circuits 220. Accordingly, DC blocking capacitors 302 block DC signals and only pass AC signals to switching circuits 220.

By coupling DC blocking capacitors 302 as shown in FIG. 3, the number of DC blocking capacitors 302 can be reduced (relative to known IPG circuitry 200). For example, IPG circuitry 300, like known IPG circuitry 200 includes four switching circuits 220. In the example embodiment, each switching circuit 220 is a multiplexer circuit. Alternatively, any suitable switching circuit 220 may be used, and IPG circuitry 300 may include any suitable number of switching circuits 220 and output channels 222.

In known IPG circuitry 200, four switching circuits 220 require four DC blocking capacitors 230. However, as shown in FIG. 3, only two DC blocking capacitors 302 are required for four switching circuits 220 in IPG circuitry 300. Thus, locating DC blocking capacitors 302 between anode node 204/cathode node 206 and switching circuits 220 reduces the number of DC blocking capacitors 302 required.

Further, in IPG circuitry 300, the number of DC blocking capacitors 302 required does not vary with the number of switching circuits 220. For example, even if IPG circuitry 300 included eight switching circuits 220, only two DC blocking capacitors 302 would still be required. Those of skill in the art will appreciate that the configuration shown in FIG. 3 can also be expanded to embodiments including multiple stimulation engines (e.g., including multiple sets of anode nodes 204 and corresponding cathode nodes 206) for creating multi-frequency and/or complex waveforms. Specifically, each stimulation engine can include one DC blocking capacitor coupled between the at least one anode node and the switching circuits, and one DC blocking capacitor coupled between the at least one cathode node and the switching circuits.

In the example embodiment, to couple DC blocking capacitors 302 as shown in FIG. 3, each of anode node 204 and cathode node 206 include an input pad and an output pad (not shown). Notably, using the input and output pads, the voltage across each DC blocking capacitor 302 may be directly monitored, which is not possible in known IPG circuitry 200. This provides enhanced stimulation diagnostic capability for IPG circuitry 300.

Each DC blocking capacitor 302 may have a capacitance, for example, in a range between approximately 10 and 30 µF. Alternatively, DC blocking capacitors 302 may have any suitable capacitance. Although two DC blocking capacitors 302 are shown in FIG. 3, in some embodiments only a single DC blocking capacitor 302 may be used. However, using two DC blocking capacitors 302 provides protection in the event that one of DC blocking capacitors 302 fails.

As described above, DC blocking capacitors 302 prevent DC signals from anode node 204 and cathode node 206 from reaching switching circuits 220. However, switching circuits 220 are typically coupled to ground and control voltages, and shorts to ground and/or the control voltages may result in potential DC leakage to patient tissue 202. For example, without a sufficient discharging scheme, an output fault on one of switching circuits 220 that shorts ground to patient tissue 202 may allow for voltage to build up on an electrode/tissue interface.

Accordingly, modifications to IPG circuitry 300 may be made to prevent such DC leakage, and to maintain any DC leakage at an acceptably low level in the event of single-fault failures in switching circuits 220. These modifications are generally referred to herein as 'mitigation circuitry'. Similar modifications may also be made for diagnostic switches (e.g., multiplexers) coupled directly to an electrode output.

Specifically, using the embodiments described herein, the flow of DC through output channels 222 is prevented during a single fault failure condition. That is, the embodiments described herein prevent a single DC leakage fault on one of output channels 222 from rendering the IPG non-functional. Instead, in the event one output channel 222 fails, that channel may be replaced with a neighboring channel to continue operation of the IPG. By automatically detecting when one or more switching circuits 220 have failed due to DC leakage (as described herein), the need for electrode reprogramming may be communicated by the IPG to the patient and/or clinician.

Figure 4:
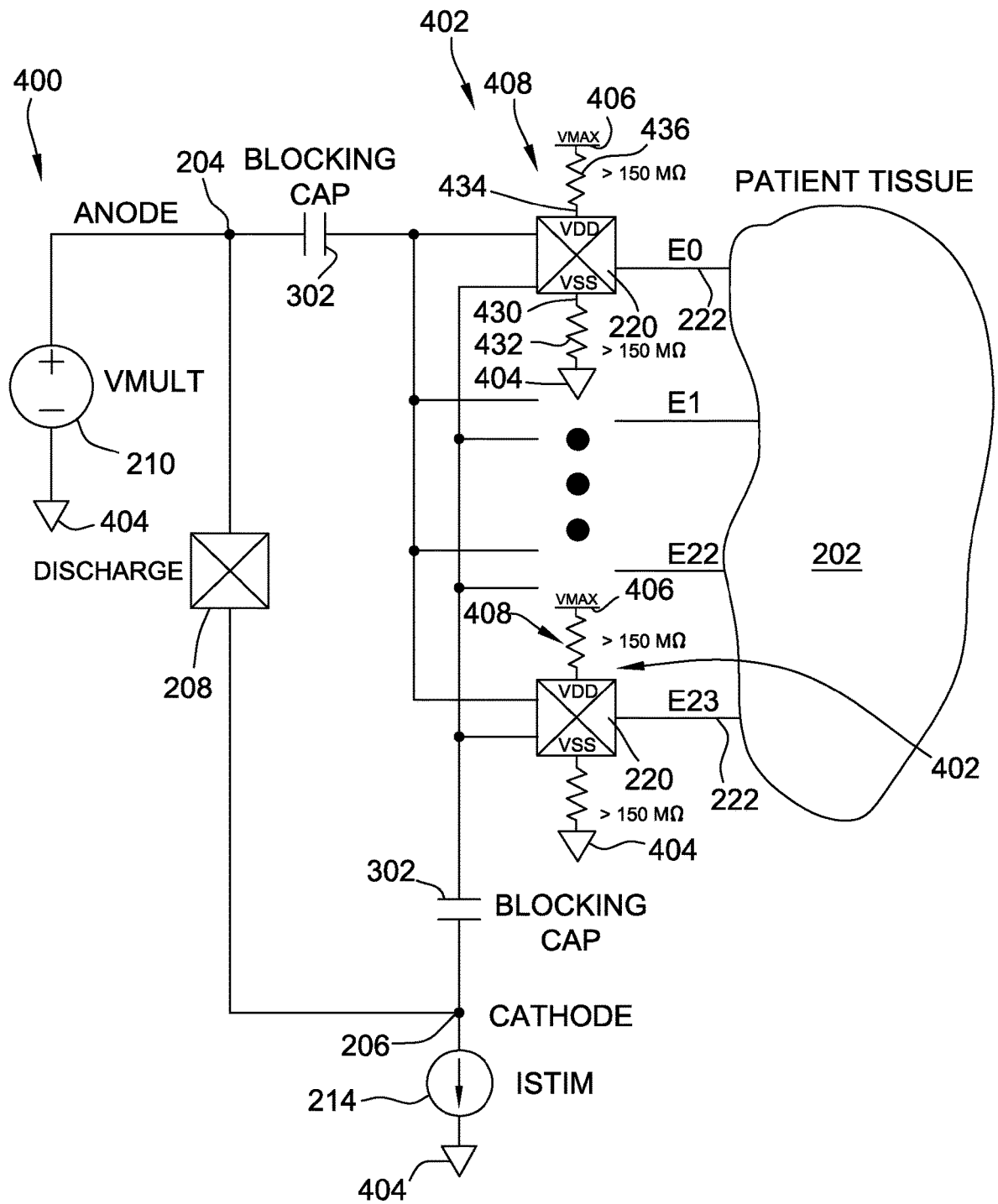
FIG. 4 is a circuit diagram of another embodiment of IPG circuitry in accordance with the present disclosure.

FIG. 4 is a circuit diagram of another embodiment of IPG circuitry 400 in accordance with the present disclosure. Unless otherwise indicated, components in IPG circuitry 400 are substantially similar to components in IPG circuitry 300 given the same reference numeral. IPG circuitry 400 includes mitigation circuitry 402, as described in detail herein.

As discussed above, switching circuits 220 are each connected to ground 404 and a control voltage 406 (VMAX). Further, leakage to ground 404 and/or control voltage 406 is a concern, as it may result in DC leakage to patient tissue 202. In the embodiment shown in FIG. 4, IPG circuitry 400 includes twenty-four switching circuits 220. Alternatively, IPG circuitry 400 may include any suitable number of switching circuits 220.

In IPG circuitry 400, to protect against DC leakage resulting from such faults, each switching circuit 220 is coupled to ground 404 and control voltage 406 using high-resistance circuitry 408. Specifically, for each switching circuit 220, a first power supply terminal 430 (VSS) is coupled to ground 404 through a first resistance circuit 432, and a second power supply terminal 434 (VMAX) is coupled to control voltage 406 through a second resistance circuit 436.

As described herein, high-resistance circuitry 408 provides a very high effective DC series resistance for the ground 404 and control voltage 406 connections. For example, as shown in FIG. 4, high-resistance circuitry 408 may have an effective series resistance of greater than 150 megaohms (MΩ). High-resistance circuitry 408 for each switching circuit 220 imposes upper safe limits on the amount of DC leakage that can flow to output channels 222 during a single fault condition. High-resistance circuitry 408 may be implemented, for example, using high-resistance continuous-time DC connections or effective high-resistance DC connections provided by switched capacitor networks, as described herein.

In the embodiments described herein, DC leakage through an output channel 222 only renders that particular channel 222 inoperable for stimulation delivery. That is, in the event one output channel 222 fails, remaining output channels 222 may still be used to provide stimulation to patient tissue 202. This is achievable by isolating each switching circuit 220 and output channel 222 from the remaining switching circuits 220 and output channels 222. For example, in at least some of the embodiments described herein, each switching circuit 220 has its own independent high-resistance DC power supply connection.

Figure 5:
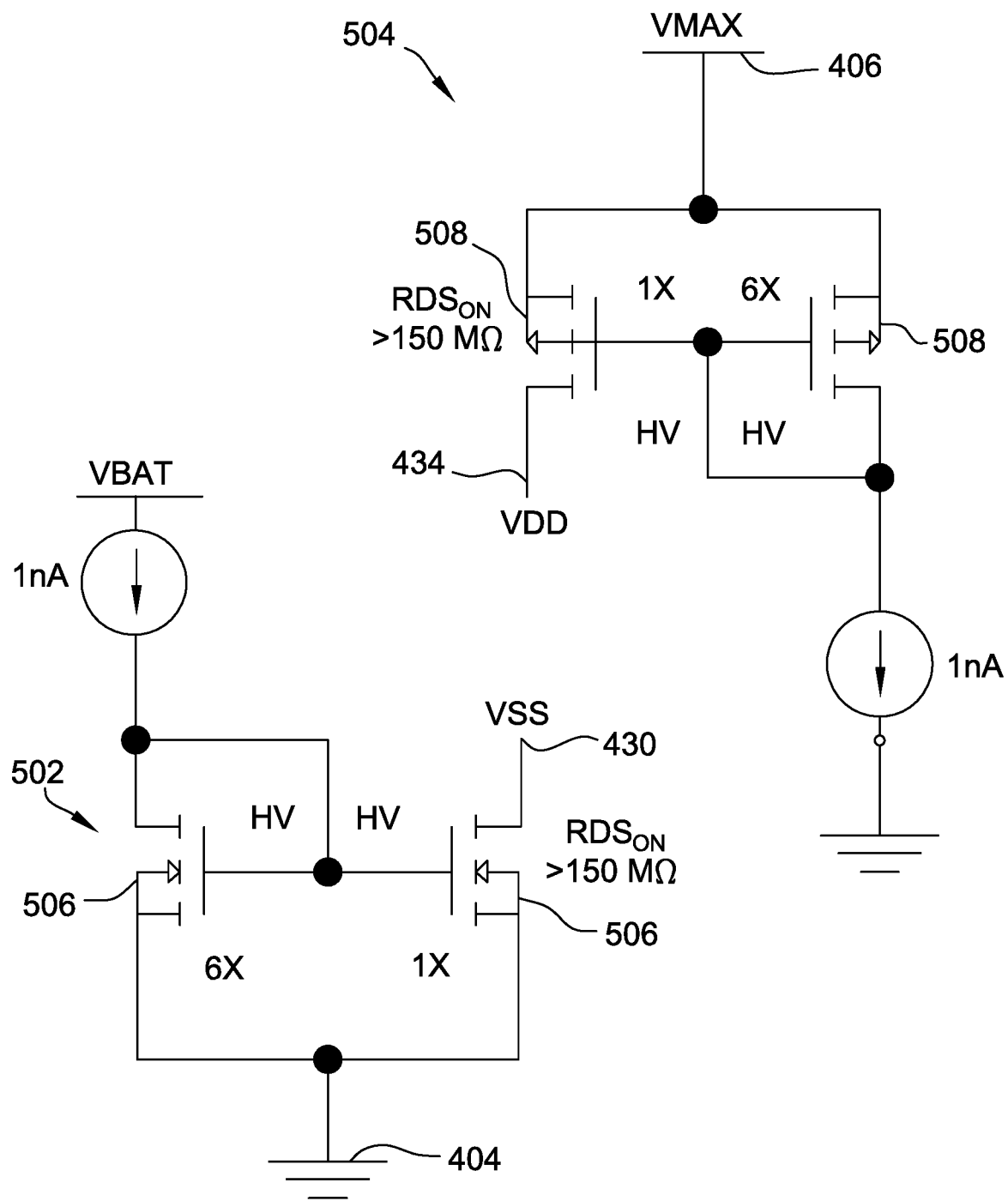
FIG. 5 is a circuit diagram of one embodiment of a first resistance circuit and a second resistance circuit in accordance with the present disclosure.
Figure 6:
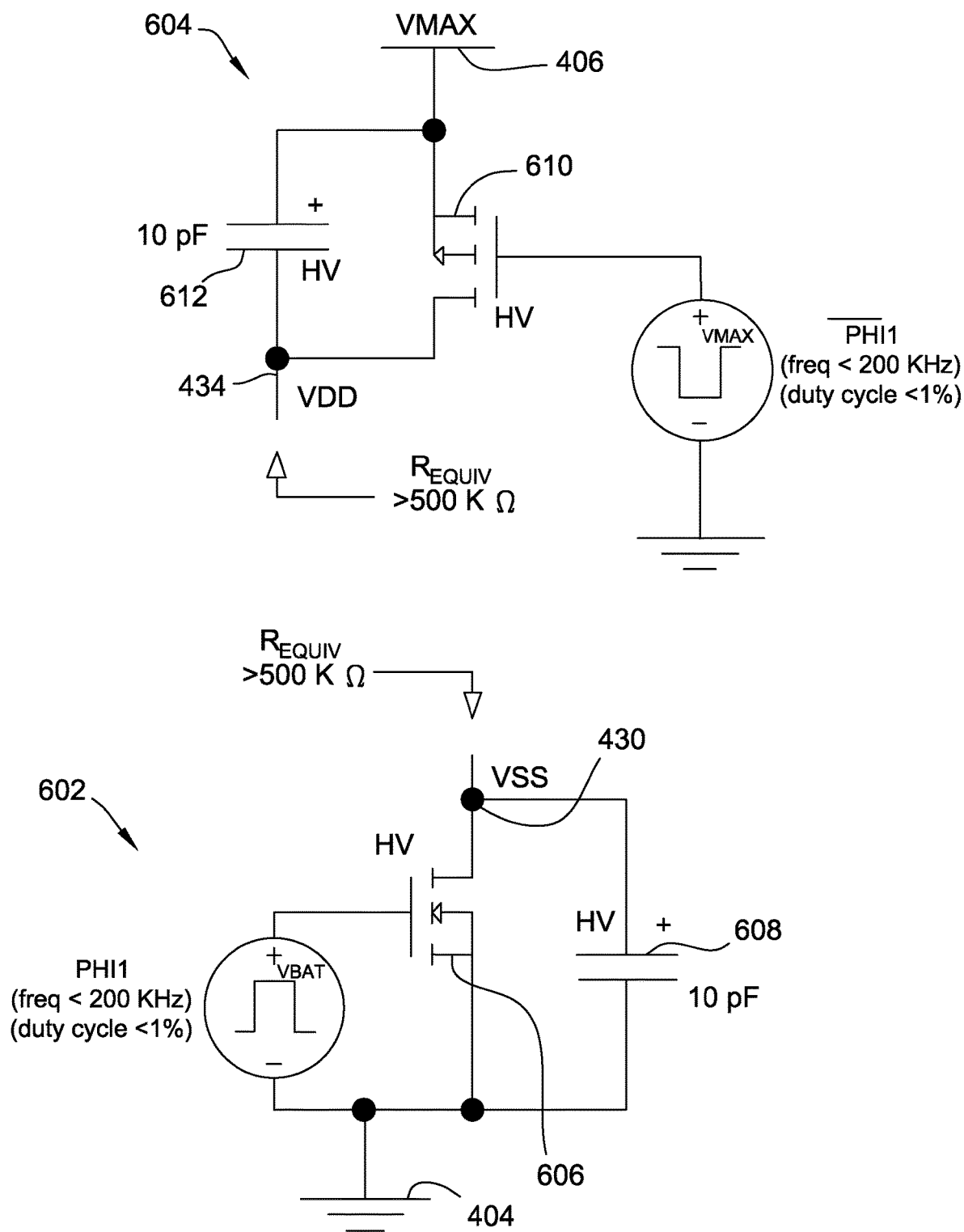
FIG. 6 is a circuit diagram of another embodiment of a first resistance circuit and a second resistance circuit in accordance with the present disclosure.

To prevent a single fault DC leakage from exceeding 2 μA, with anode voltages as high as 15 V, power supply resistances should be at least 15 V/2 μA, or 7.5 MΩ. To provide a safety margin of a factor of twenty, and thus limit the DC leakage to 0.1 μA or less, the power supply resistances may be set at least at 150 MΩ in at least some of the embodiments described herein. This level of resistance is achievable via continuous-time DC biasing circuitry operating in a sub-threshold regime (as shown in FIG. 5), or via switched capacitor circuitry (as shown in FIG. 6). Those of skill in the art will appreciate that other high-resistance or current-limiting circuitry may be used alternatively.

FIG. 5 is a circuit diagram of one embodiment of a first resistance circuit 502 and a second resistance circuit 504. First resistance circuit 502 and second resistance circuit 504 may be used to implement first resistance circuit 432 and second resistance circuit 436, respectively (both shown in FIG. 4). First resistance circuit 502 and second resistance circuit 504 are implemented using continuous-time DC biasing circuitry, as described herein.

In the embodiment shown in FIG. 5, first resistance circuit 502 includes NMOS transistors 506 that form a high-resistance connection to ground 404. Further, second resistance circuit 504 includes PMOS transistors 508 that form a high resistance connection to control voltage 406.

Both first and second resistance circuits 502 and 504 operate transistors 506 and 508 in a conduction region which is considered "weak inversion" or "sub-threshold", whereby transistors 506 and 508 conduct current at Gate-to-Source voltages (VGS) which are appreciably below the respective transistors' threshold voltages (i.e. VTN and VTP). The designation "HV" indicates that transistors 506 and 508 have "thick" Gate oxides, which are typically capable of handling as much as 18V without damage in Neurostimulator IPGs. This HV capability ensures that transistors 506 and 508 will not be catastrophically damaged during normal IPG operation and usage, which under transient conditions or under leakage conditions might put as much as 15V across the Gate/Drain terminals of transistors 506 and 508.

With 1 nanoamp (nA) DC bias currents as shown in FIG. 5 (generated elsewhere within the IPG system), the bias currents flowing through the 6× sized devices by design will establish DC VGS bias voltages on each of the respective 6× NMOS and PMOS transistors 506 and 508. In this embodiment, both the 6× NMOS and PMOS transistors 506 and 508 are physically sized to an appropriate Width, Length, and Width-to-Length ratio (W, L, and W/L, respectively) so that the 6× devices conduct at current densities which cause them to operate in the sub-threshold—i.e. at a VGS<VT. Thus, the 6× NMOS transistor 506 will operate at a VGSN voltage which is less than VTN, and the 6× PMOS transistor 508 will operate at a VGSP voltage which has |VGSP|<|VTP| (note that magnitudes of the PMOS voltages are generally used, since both VGSP and VTP voltages are negative values).

The current density required for deep sub-threshold operation is generally less than or equal to 10 nA/square (where a "square" is the W/L ratio). Thus, the 6× NMOS and PMOS transistors 506 and 508 are sized with W and L dimensions so that the total W/L ratio is greater than or equal to 0.1 when using bias currents of 1 nA, in order to achieve sub-threshold operation.

The on-resistance of the 1× NMOS transistor 506 will be determined by the VGSN voltage set by the 6× NMOS transistor 506, and the on-resistance of the 1× PMOS transistor 508 will be determined by the VGSP voltage set by the 6× PMOS transistor 508. So long as no leakage currents flow through the 1× NMOS and 1× PMOS transistors 506 and 508, their $RDS_{ON}$ on-resistances can be determined via the following equation when they operate in sub-threshold:

$$RDS_{ON} = (kT/q)/IDS_{SAT}$$

where k is Boltzman's constant ($1.381 \times 10^{-23}$), T is 310 Kelvin (K) (equivalent to 37° C., body temperature), $q=1.602 \times 10^{-19}$ (i.e., the charge of an electron), and $IDS_{SAT}=\frac{1}{6}*1$ nA, $RDS_{ON}=160$ MΩ which is fairly close to the 150 MΩ target value.

The current density required for deep sub-threshold operation is generally less than or equal to 10 nA/square (where a "square" is the W/L ratio). Thus, the 6× NMOS and PMOS transistors 506 and 508 are sized with W and L dimensions so that the total W/L ratio is greater than or equal to 0.1 when using bias currents of 1 nA, in order to achieve sub-threshold operation.

However, MOS transistors 506 and 508 can maintain such an on-resistance only when a Drain-to-Source voltage (VDS) is much less than 100 millivolts (mV), typically ~25 mV or less, which will occur only if the Drain-to-Source current (IDS) through each of the devices is well below ⅙ nA or 167 picoamps (pA) for the above example (due to the 6:1 current mirror ratio of the 6× transistors relative to the 1× output transistors). If a leakage current greater than 167 pA tries to flow through either of the 1× NMOS or 1× PMOS transistors 506 and 508, the transistor on-resistance will increase appreciably, and the device may even "saturate" in current, which may cause the VDS voltage to be much greater than 100 mV, which will make a very poor DC connection to VSS or VMAX.

However, leakages for switching circuits 220 can readily reach levels much greater than 167 pA, even under normal conditions. Thus, to improve manufacturability and performance, in this embodiment, the 1× NMOS and PMOS transistors 506 and 508 are capable of handling much more substantial levels of leakage (i.e. much greater than 167 pA) but which are still less than 1 μA. Thus, the NMOS and PMOS circuit arrangements may be "scaled up" in size (i.e. larger W, smaller L, and W/L ratios) and/or bias currents (i.e. bias currents larger than 1 nA), so that the "saturation" current of the 1× transistors 506 and 508 is appreciably closer to (but still somewhat less than) the maximum 1 μA leakage so as to provide "safety margin".

An alternative $RDS_{ON}$ target for the 1× NMOS and PMOS transistors 506 and 508 is 267 KΩ, which would still allow the devices to behave with a maximum "saturation" current of ~0.1 μA (i.e. still providing a leakage safety margin of 10× below the 1 μA leakage limit for each switching circuit 220).

Because the "scaled up" 1× NMOS and 1× PMOS transistors 506 and 508 still will not allow more than 0.1 μA of current to flow to VSS/VMAX, respectively, they inherently mitigate single-fault current leakage failures in switching circuits 220. However, it may still be desirable to monitor if/when there exists such a fault condition, so that a defective switching circuit 220 can be disabled. In one embodiment, that monitoring is accomplished using two simple Low Voltage (LV) analog inverting amplifier circuits that draw very low power, with their inputs connected to each of the VSS and VDD output nodes of first resistance circuit 502 and second resistance circuit 504, respectively. The outputs of the analog inverting amplifier circuits may be sent as digital error signals to a control block that disconnects the GND and VMAX power supply terminals (e.g., first power supply terminal 430 and second power supply terminal 434) from first resistance circuit 502 and second resistance circuit 504, and also disables gates of the corresponding switching circuit 220 to put it in an OFF state.

FIG. 6 is a circuit diagram of another embodiment of a first resistance circuit 602 and a second resistance circuit 604. First resistance circuit 602 and second resistance circuit 604 may be used to implement first resistance circuit 432 and second resistance circuit 436, respectively (both shown in FIG. 4). First resistance circuit 602 and second resistance circuit 604 are implemented using switched-capacitor circuitry, as described herein.

In the embodiment shown in FIG. 6, first resistance circuit 602 includes a High Voltage (HV) NMOS switch 606 and first HV capacitor 608, and second resistance circuit includes a HV PMOS switch 610 and HV capacitor 612.

As will be appreciated by those of skill in the art, regular and periodic discharging of a capacitor via a switch causes the steady-state behavior of the capacitor to act effectively like a resistance. The effective on-resistance of a switched-capacitor network is determined by starting with the I=C*dV/dt equation relating the current and voltage of a capacitor, and then re-arranging the equation in the form to get dV/I for the effective resistance. Thus, the steady-state or effective on-resistance of a switched-capacitor circuit is given by:

$$R_{ON\_EFF}=dV/I=dt/C$$

However, with HV NMOS and PMOS switches 606 and 610 switching at a frequency of F=1/dt (note that the time, dt, is equivalent to a period of clock signals driving the gates of switches 606 and 610) to discharge HV capacitors 608 and 612, the above equation becomes:

$$R_{ON\_EFF}=1/(F*C)$$

Accordingly, if a 50 mV build-up of voltage across each capacitor 608 and 612 is tolerable when 0.1 μA leakage currents flow through each of them, then the $R_{ON\_EFF}$ will be much more than 50 mV/0.1 μA or much more than 500 KΩ (which is comparable to the on-resistance value for the continuous-time implementation discussed above). To achieve this value of $R_{ON\_EFF}$ with 10 μF HV capacitors 608 and 612 requires each of the NMOS and PMOS switches 606 and 610 to be turned on at a frequency of F less than or equal to 1/(500 KΩ*10 pF), or 200 KHz, which is a feasible clocking frequency in a neurostimulator IPG. Higher clock frequencies may be used if smaller HV capacitance values are desirable, so long as the $R_{ON\_EFF}$ value is kept at 500 KΩ or higher. Note that, in order to keep the current flow through NMOS and PMOS switches 606 and 610 at a minimum, the duty cycle of a clock driving their gates should be relatively low (e.g., approximately 1%).

If the leakage through either of first resistance circuit 602 and second resistance circuit 604 exceeds 0.1 μA for any particular switching circuit 220, however, then the voltage across HV capacitor 608 or 612 will exceed 50 mV, and output channel 222 should be disabled and the first resistance circuit 602 and second resistance circuit 604 open-circuited.

Accordingly, in this embodiment, to ensure that leakage does not exceed 0.1 μA, two HV comparators (not shown) may be used to monitor the voltages across each HV capacitor 608 and 612. If one of the comparators detects that the HV capacitor voltage exceeds 50 mV, then that comparator toggles its output state to send an error signal to other digital control circuitry, which results in disconnecting ground 404 from first resistance circuit 602 and disconnecting control voltage 406 from second resistance circuit 604, and disabling clocks going to the HV NMOS and PMOS switches 606 and 610 (as well as leaving them in an OFF state). The 50 mV comparator detection threshold is one example, and is feasible as CMOS Comparators typically have input offsets well under 50 mV (i.e. the small comparator offset won't compromise the "safety margin" of the switched-capacitor circuitry to ensure that leakages are well under 1 uA).

Figure 7:
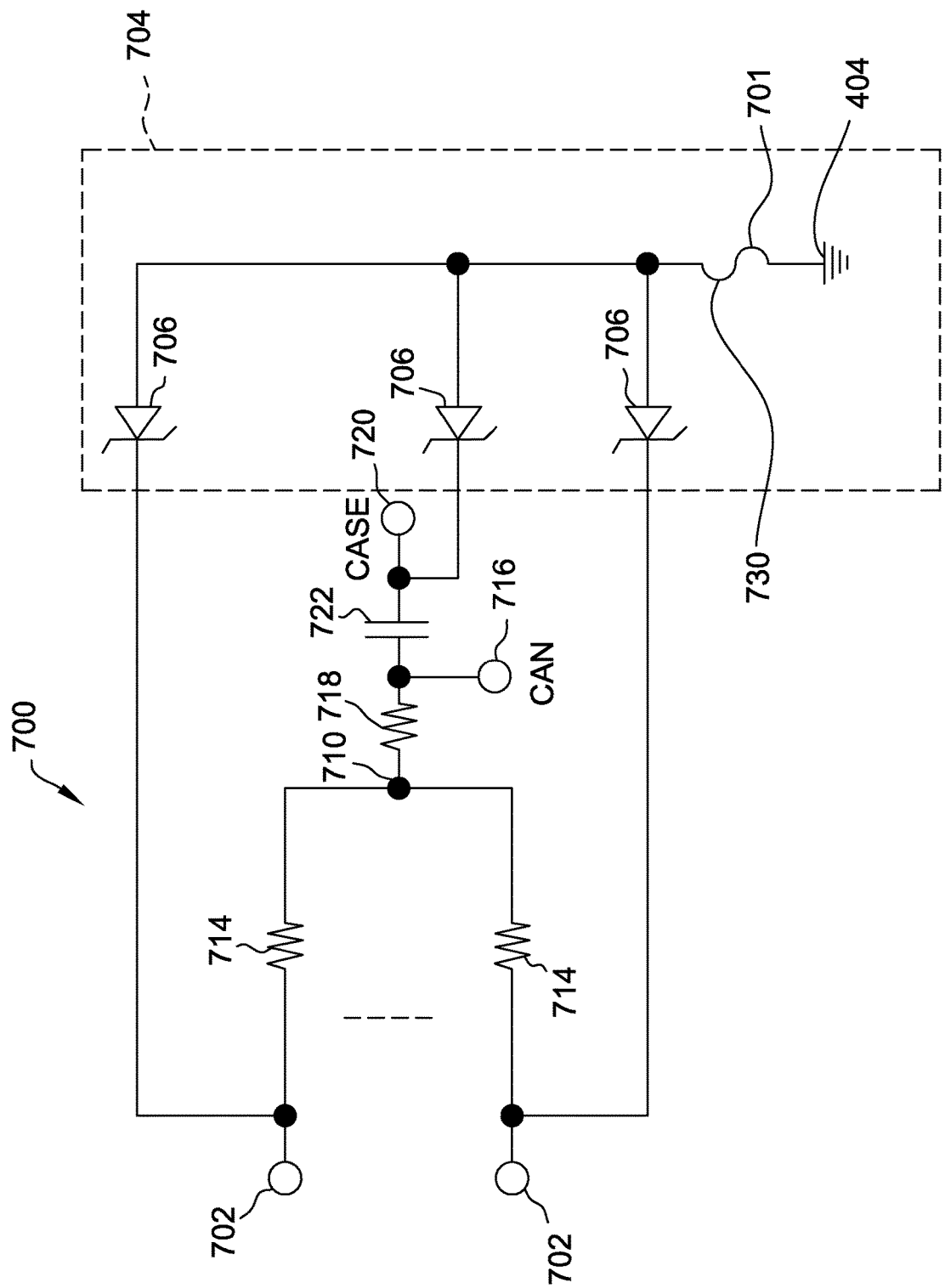
FIG. 7 is a circuit diagram of another embodiment of IPG circuitry including mitigation circuitry in accordance with the present disclosure.

FIG. 7 is a circuit diagram of IPG circuitry 700 illustrating mitigation circuitry 701 in another embodiment. IPG circuitry 700 includes an IPG case connection 720, a plurality of electrodes 702, and protection circuitry 704. Protection circuitry 704 includes a plurality of protection Zener diodes 706 electrically coupled via a destructible conductive link 730 to ground 404 (e.g., a negative battery terminal). Each electrode 702 and IPG case connection 720 are electrically coupled to ground 404 via destructible conductive link 730 through an associated protection Zener diode 706.

As shown in FIG. 7, each electrode 702 is electrically coupled through patient tissue to a theoretical common node 710 through a respective tissue resistance 714. Further, common node 710 is electrically coupled to a can electrode connection 716 through a tissue resistance 718, and can electrode connection 716 is electrically coupled to IPG case connection 720 through a capacitor 722. IPG case connection 720 is electrically coupled to ground 404 via destructible conductive link 730 through a protection Zener diode 706.

In at least some known systems, protection Zener diodes 706 are directed coupled to ground 404. As will be appreciated by those of skill in the art, protection Zener diodes 706 provide electrostatic discharge (ESD) and defibrillation protection. Notably, with DC blocking capacitors removed from the output channels, it is desirable to mitigate excess DC leakages through protection Zener diodes 706, because protection Zener diodes 706 are directly connected to electrodes 702.

Accordingly, in the embodiment shown in FIG. 7, mitigation circuitry 701 includes a destructible conductive link 730 coupled between protection Zener diodes 706 and ground 404. Destructible conductive link 730 may be, for example, a fuse that can be blown to remove the electrical connection between protection Zener diodes 706 and ground 404. Alternatively, destructible conductive link 730 may be a conductive trace that can be severed using a laser cut.

The connection between protection Zener diodes 706 and ground 404 prevents static damage from occurring during IPG circuit assembly before enclosing the assembled circuitry within a titanium can. Notably, once the assembled circuitry is enclosed within the can, the static protection relative to ground 404 is no longer needed. Accordingly, in this embodiment, the destructible conductive link 730 is intact during assembly. However, just prior to inserting IPG circuitry 700 into the can, the destructible conductive link 730 is destroyed (e.g., by blowing the fuse or severing the conductive trace), disconnecting protection Zener diodes 706 from ground 404.

Disconnecting protection Zener diodes 706 from ground 404 alleviates their DC leakage to electrodes 702. In this configuration, any DC leakage conduction path through one of protection Zener diodes 706 will merely conduct to the other protection Zener diodes 706. Further, once a stimulation lead is connected between the IPG and patient tissue, all electrodes 702 will DC bias at the same potential and will already have DC connectivity between one another, this making innocuous any small DC flow between electrodes 702 due to a leaky protection Zener diode 706. Further, once destructible conductive link 730 is destroyed protection Zener diodes 706 need only protect electrodes 702 from over-voltage conditions relative to the can and other electrodes, and connection to ground 404 is no longer necessary.

In some embodiments, additional DC connections are capable of being made to output channels 222. For example, in some embodiments, a diagnostic switch for measuring residual voltages on electrodes after stimulation may be connected to the IPG circuitry. Accordingly, mitigation circuitry similar to the embodiments described above may be used in such embodiments. For example, high-resistance circuitry similar to that described in association with FIGS. 4-6 may be used for diagnostic switches.

As described above, connecting DC blocking capacitors between at least one anode node/cathode node and switching devices may necessitate including additional mitigation circuitry in the IPG circuitry to eliminate DC leakage. Notably, relative to including DC blocking capacitors on the output channels, the mitigation circuitry is relatively inexpensive and generally takes up much less space. Accordingly, even though locating DC blocking capacitors as described herein may result in adding additional mitigation circuitry, the resulting IPG circuitry is still less expensive and has a smaller footprint than at least some known IPG circuitry including DC blocking capacitors on each of the output channels.

The embodiments described herein provide systems and methods for improved circuitry for an implantable pulse generator (IPG) of a neurostimulation system. The circuitry includes at least one anode node, at least one cathode node, a plurality of switching circuits, each switching circuit coupled to the at least one anode node and the at least one cathode node, and a plurality of output channels, each output channel coupled between an associated switching circuit and at least one electrode. The circuitry further includes a first DC blocking capacitor coupled between the at least one anode node and the plurality of switching circuits, a second DC blocking capacitor coupled between the at least one cathode node and the plurality of switching circuits. The circuitry further includes mitigation circuitry operable to limit DC leakage from the plurality of switching circuits through the plurality of output channels.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. Circuitry for an implantable pulse generator (IPG) of a neurostimulation system, the circuitry comprising:
    at least one anode node;
    at least one cathode node;
    a plurality of switching circuits, each switching circuit coupled to the at least one anode node and the at least one cathode node;
    a plurality of output channels, each output channel coupled between an associated switching circuit and at least one electrode;
    a first DC blocking capacitor coupled between the at least one anode node and the plurality of switching circuits;
    a second DC blocking capacitor coupled between the at least one cathode node and the plurality of switching circuits; and
    mitigation circuitry operable to limit DC leakage from the plurality of switching circuits through the plurality of output channels, at least a portion of the mitigation circuitry electrically coupled between the plurality of output channels and ground.

2. The circuitry of claim 1, wherein the mitigation circuitry comprises high-resistance circuitry coupling each of the plurality of switching devices to ground and a control voltage.

3. The circuitry of claim 2, wherein the high-resistance circuitry comprises:
    a first resistance circuit coupling a first power supply terminal of a first switching device to ground; and
    a second resistance circuit coupling a second power supply terminal of the first switching device to the control voltage.

4. The circuitry of claim 3, wherein the first and second resistance circuit comprise continuous-time DC biasing circuitry.

5. The circuitry of claim 3, wherein the first and second resistance circuit comprise switched capacitor circuitry.

6. The circuitry of claim 1, further comprising protection circuitry comprising a plurality of protection Zener diodes, wherein the mitigation circuitry comprises a destructible conductive link coupled between the plurality of protection Zener diodes and ground.

7. The circuitry of claim 6, wherein the destructible conductive link comprises a fuse.

8. A neurostimulation system comprising:
an implantable pulse generator (IPG) ground;
an IPG case;
a stimulation lead comprising a plurality of electrodes; and
an IPG coupled to the IPG ground, the IPG case, and the stimulation lead, the IPG comprising circuitry that comprises:
at least one anode node;
at least one cathode node;
a plurality of switching circuits, each switching circuit coupled to the at least one anode node and the at least one cathode node;
a plurality of output channels, each output channel coupled between an associated switching circuit and at least one electrode;
a first DC blocking capacitor coupled between the at least one anode node and the plurality of switching circuits;
a second DC blocking capacitor coupled between the at least one cathode node and the plurality of switching circuits; and
mitigation circuitry operable to limit DC leakage from the plurality of switching circuits through the plurality of output channels, at least a portion of the mitigation circuitry electrically coupled between the plurality of output channels and ground.

9. The neurostimulation system of claim 8, wherein the mitigation circuitry comprises high-resistance circuitry coupling each of the plurality of switching devices to ground and a control voltage.

10. The neurostimulation system of claim 9, wherein the high-resistance circuitry comprises:
a first resistance circuit coupling a first power supply terminal of a first switching device to ground; and
a second resistance circuit coupling a second power supply terminal of the first switching device to the control voltage.

11. The neurostimulation system of claim 10, wherein the first and second resistance circuit comprise continuous-time DC biasing circuitry.

12. The neurostimulation system of claim 10, wherein the first and second resistance circuit comprise switched capacitor circuitry.

13. The neurostimulation system of claim 8, wherein the circuitry further comprises protection circuitry comprising a plurality of protection Zener diodes, and wherein the mitigation circuitry comprises a destructible conductive link coupled between the plurality of protection Zener diodes and ground.

14. The neurostimulation system of claim 13, wherein the destructible conductive link comprises a fuse.

15. A method of assembling circuitry for an implantable pulse generator (IPG) of a neurostimulation system including an IPG ground, a plurality of electrodes, and an IPG case, the method comprising:
providing at least one anode node and at least one cathode node;
electrically coupling a plurality of switching devices to the at least one anode node and the at least one cathode node;
electrically coupling each of a plurality of output channels between an associated switching device and at least one electrode;
electrically coupling a first DC blocking capacitor between the at least one anode node and the plurality of switching circuits;
electrically coupling a second DC blocking capacitor between the at least one cathode node and the plurality of switching circuits; and
implementing migration circuitry operable to limit DC leakage from the plurality of switching circuits through the plurality of output channels, at least a portion of the mitigation circuitry electrically coupled between the plurality of output channels and ground.

16. The method of claim 15, wherein implementing mitigation circuitry comprises coupling each of the plurality of switching devices to ground and a control voltage using high-resistance circuitry.

17. The method of claim 16, wherein coupling each of the plurality of switching devices to ground and the control voltage using high-resistance circuitry comprises:
coupling a first power supply terminal of a first switching device to ground using a first resistance circuit; and
coupling a second power supply terminal of the first switching device to the control voltage using a second resistance circuit.

18. The method of claim 17, wherein the first and second resistance circuit include continuous-time DC biasing circuitry.

19. The method of claim 17, wherein the first and second resistance circuit include switched capacitor circuitry.

20. The method of claim 15, wherein implanting mitigation circuitry comprises:
coupling a plurality of protection Zener diodes to ground through a destructible conductive link; and
destroying the destructible conductive link prior to enclosing the circuitry in a can.

* * * * *